(12) United States Patent
Sakai et al.

(10) Patent No.: US 9,310,342 B2
(45) Date of Patent: Apr. 12, 2016

(54) LIQUID CHROMATOGRAPHY APPARATUS AND LIQUID CHROMATOGRAPHY

(75) Inventors: Toshikatsu Sakai, Kyoto (JP); Akira Sezaki, Kyoto (JP); Takeshi Takagi, Kyoto (JP); Takuya Yotani, Kyoto (JP); Makoto Takahara, Kyoto (JP); Takayuki Oka, Kyoto (JP)

(73) Assignees: ARKRAY, Inc., Kyoto-shi (JP); Sekisui Medical Co., Ltd., Chuo-ku (JP)

( * ) Notice: Subject to any disclaimer, the term of this patent is extended or adjusted under 35 U.S.C. 154(b) by 652 days.

(21) Appl. No.: 13/122,602

(22) PCT Filed: Oct. 6, 2009

(86) PCT No.: PCT/JP2009/067369
§ 371 (c)(1),
(2), (4) Date: Apr. 5, 2011

(87) PCT Pub. No.: WO2010/041637
PCT Pub. Date: Apr. 15, 2010

(65) Prior Publication Data
US 2011/0186511 A1     Aug. 4, 2011

(30) Foreign Application Priority Data

Oct. 7, 2008  (JP) .................................. 2008-260465

(51) Int. Cl.
*G01N 30/24*        (2006.01)
*G01N 30/26*        (2006.01)
(Continued)

(52) U.S. Cl.
CPC ................ *G01N 30/24* (2013.01); *G01N 30/26* (2013.01); *B01D 15/16* (2013.01); *G01N 30/74* (2013.01);
(Continued)

(58) Field of Classification Search
CPC . G01N 30/24; G01N 30/26; G01N 2030/207; G01N 2030/8822; G01N 2030/202; G01N 30/74; G01N 2030/201; B01D 15/16
USPC ........................................ 210/635, 656, 198.2
See application file for complete search history.

(56) References Cited

U.S. PATENT DOCUMENTS 3,504,799 A * 4/1970 Ogle .......................... 210/198.2
RE29,454 E * 10/1977 Ashmead et al. ................. 222/1
(Continued)

FOREIGN PATENT DOCUMENTS

DE        4124058 A1      1/1992
EP        2083274    *    7/2009
(Continued)

OTHER PUBLICATIONS

PTO Translation No. 12-6319 of Japan U.S. Pat. No. 2003107064.*
(Continued)

*Primary Examiner* — Ernest G Therkorn
(74) *Attorney, Agent, or Firm* — Fox Rothschild LLP

(57) ABSTRACT

A liquid chromatography apparatus is provided with a sample preparation unit, a column that separates components of a sample, an eluent supplier that includes a feeder for supplying eluents to the column, a flow path directional valve capable of introducing fixed amounts of the sample and the eluents to the column, an analyzer for analyzing a test solution composed of the sample components separated by the column and one of the eluents, and a controller, wherein the eluent supplier supplies the eluents to the flow path directional valve in an unmixed state. As a result of employing this configuration, analysis time is shortened and eluent consumption is reduced.

2 Claims, 12 Drawing Sheets

(51) Int. Cl.
G01N 30/20 (2006.01)
G01N 30/88 (2006.01)
B01D 15/16 (2006.01)
G01N 30/74 (2006.01)

(52) U.S. Cl.
CPC .... *G01N 2030/201* (2013.01); *G01N 2030/202* (2013.01); *G01N 2030/207* (2013.01); *G01N 2030/8822* (2013.01)

(56) References Cited

U.S. PATENT DOCUMENTS

| | | | | |
|---|---|---|---|---|
| 4,116,046 | A | * | 9/1978 | Stein .................... 73/61.55 |
| 4,158,630 | A | * | 6/1979 | Stearns .................. 210/198.2 |
| 4,274,967 | A | * | 6/1981 | Snyder .................... 210/659 |
| 4,478,713 | A | * | 10/1984 | Girot et al. ............... 210/101 |
| 4,595,496 | A | * | 6/1986 | Carson .................... 210/101 |
| 4,699,718 | A | * | 10/1987 | Jones et al. ............... 210/659 |
| 4,728,434 | A | * | 3/1988 | Trafford ................... 210/656 |
| 4,879,039 | A | * | 11/1989 | Takahashi et al. ........... 210/635 |
| 5,135,718 | A | * | 8/1992 | Kawaguchi et al. ........... 422/70 |
| 5,348,649 | A | * | 9/1994 | Mizuno et al. ............. 210/198.2 |
| 5,358,639 | A | * | 10/1994 | Yasuda et al. .............. 210/635 |
| 5,468,643 | A | | 11/1995 | Su et al. |
| 5,674,388 | A | * | 10/1997 | Anahara ................... 210/198.2 |
| 5,730,867 | A | * | 3/1998 | Drew et al. ............... 210/198.2 |
| 6,344,172 | B1 | * | 2/2002 | Afeyan et al. ............... 422/70 |
| 2005/0194318 | A1 | | 9/2005 | Ozbal et al. |
| 2008/0134804 | A1 | | 6/2008 | Maeda et al. |
| 2008/0245136 | A1 | * | 10/2008 | Gerhardt et al. ............ 73/61.56 |

FOREIGN PATENT DOCUMENTS

| | | | |
|---|---|---|---|
| JP | 5-281222 | A | 10/1993 |
| JP | 2003-014719 | A | 1/2003 |
| JP | 2003-107064 | A | 4/2003 |
| JP | 2003-247987 | A | 9/2003 |
| JP | 2007-240500 | A | 9/2007 |
| WO | WO-93/07168 | A2 | 4/1993 |
| WO | 2008035748 | A1 | 3/2008 |

OTHER PUBLICATIONS

PTO Translation No. 12-6322 of Japan U.S. Pat. No. 2003247987.*
PTO Translation No. 12-6315 of Japan U.S. Pat. No. 2003014719.*
Snyder, Introduction to Modern Liquid Chromatography, John Wiley&Sons, Inc. 1979, pp. 105-107.*
Deguchi et al., "Nanoflow Gradient Generator for Capillary High-Performance Liquid Chromatography", Analytical Chemistry, American Chemical Society, US, vol. 76, No. 5, Mar. 1, 2004, pp. 1524-1528.

* cited by examiner

US 9,310,342 B2

LIQUID CHROMATOGRAPHY APPARATUS AND LIQUID CHROMATOGRAPHY

INCORPORATION BY REFERENCE

This application is a 371 of International Application No. PCT/JP2009/067369 filed Oct. 6, 2009, which claims priority to Japanese Patent Application No. 2008-260465 filed Oct. 7, 2008, the entire contents of which being hereby incorporated herein by reference.

TECHNICAL FIELD

The present invention relates to a liquid chromatography apparatus and liquid chromatography used in blood testing, for example.

BACKGROUND ART

Liquid chromatography apparatuses have recently come to be frequently used as methods for analyzing samples in the fields of organic chemistry, biochemistry, medicine and the like. FIG. 14 shows an example of a conventional liquid chromatography apparatus (see, for example, Patent Document 1). A liquid chromatography apparatus X shown in this drawing is provided with a sample preparation unit 91, a flow path directional valve 92, a manifold 93, a feed pump 94, an analysis unit 95 and a controller 96. The sample preparation unit 91 produces a sample by diluting a sample S such as blood with a diluent Ld. A fixed amount of this sample is accumulated in an injection loop 92b of the flow path directional valve 92. When a six-way valve 92a of the flow path directional valve 92 rotates, for example, from the state shown in the drawing, the fixed amount of sample is delivered to the analysis unit 95. The analysis unit 95 has a pre-filter 95a, a column 95b and a photometric unit 95c. After a fixed amount of sample has been adsorbed by a filler of the column 95b, an eluent La is fed from the manifold 93 by the feed pump 94. This eluent La is supplied to the column 95b through the flow path directional valve 92. After having been adsorbed by the filler, the sample is desorbed by the eluent La and separated into each component within the column 95b. The photometric unit 95c is able to analyze each separated component by, for example, measuring absorbance. The controller 96 controls driving of the sample preparation unit 91, the flow path directional valve 92, the manifold 93 and the analysis unit 95.

In the analysis described above as well, other components in addition to the analysis targets remain in the column 95b. An eluent Lb is supplied from the manifold 93 to the column 95b through the flow path directional valve 92 for the purpose of washing away these other components. An eluent having, for example, a higher salt concentration than the eluent La is used for the eluent Lb. Subsequently, it is necessary to return the salt concentration of the system, including the column 95b, to that of the eluent La in order to resume the above-mentioned analysis. An eluent Lc is supplied from the manifold 93 to the column 95b through the flow path directional valve 92 in order to adjust the salt concentration. An eluent having a lower salt concentration than the eluents La and Lb is used for the eluent Lc. As a result, the salt concentration that was increased as a result of supplying the eluent Lb is lowered. The salt concentration of the column 95b can subsequently be made to be a salt concentration suitable for analysis by again supplying the eluent La.

However, hysteresis of a salt concentration Ds of the column 95b to which is sequentially supplied the eluents La, Lb and Lc is shown in FIG. 15. Namely, in the column 95b, the eluent is respectively switched from the eluent La to the eluent Lb at a time T1, from the eluent Lb to the eluent Lc at a time T2, and from the eluent Lc to the eluent La at a time T3. This switching of the eluents La, Lb and Lc is carried out by the manifold 93. Mutual mixing of the eluents La, Lb and Lc cannot be avoided during the switching operation of the manifold 93. The salt concentrations are unable to be switched instantaneously at the times T1, T2 and T3 due to the resulting turbidity, causing the hysteresis to change gradually. As a result, a considerable amount of time was required until the salt concentration of the column 95b returned to a concentration suitable for analysis. In addition, a considerable amount of eluent was consumed until the salt concentration returned to the concentration of each eluent.

Patent Document 1: Japanese Patent Application Laid-open No. 2007-240500

DISCLOSURE OF THE INVENTION

With the foregoing in view, an object of the present invention is to provide a liquid chromatography apparatus and liquid chromatography that are able to shorten analysis time and reduce eluent consumption.

A liquid chromatography apparatus provided by a first aspect of the present invention is provided with: a sample preparation unit for preparing a sample from a specimen; a column for separating components of the sample, an eluent supplier for supplying as a mobile phase two or more types of eluent to the column; a first flow path directional valve capable of introducing a fixed amount of the sample to the column and capable of introducing the eluent to the column; an analyzer for analyzing a test solution composed of the sample components separated by the column and the eluent; and a controller for controlling operation of the sample preparation unit; the eluent supplier; the first flow path directional valve and the analyzer, wherein the eluent supplier supplies two or more types of eluent to the first flow path directional valve in an unmixed state. The first and second flow path directional valves of the present invention include injection valves, directional valves such as a 3-way valve, 4-way valve, 5-way valve or 6-way valve, piston valves, plug valves, control valves and Y valves, and have a structure that enables precise control without allowing mixing of a plurality of eluents.

In a preferred embodiment of the present invention, the eluent supplier is provided with a second flow path directional valve that is able to supply first and second eluents mutually supplied to separate ports to the first flow path directional valve, and the controller carries out control so that at least a portion of the fixed amount of the second eluent accumulated in the second flow path directional valve and the first eluent subsequently introduced into the second flow path directional valve from a port different from that of the second eluent are supplied to the column through the first flaw path directional valve either during or after analysis of the test solution by supplying the first eluent to the column through the first flow path directional valve.

In a preferred embodiment of the present invention, in supplying the second eluent, in a state in which an injection loop for retaining a fixed amount of the second eluent accumulated in the second flow path directional valve is connected to a pathway leading to the first flow path directional valve, control is carried out that continues to supply the first eluent to the injection loop until all of the fixed amount of the second eluent is discharged from the injection loop.

In a preferred embodiment of the present invention, in supplying the second eluent, in a state in which an injection loop for retaining the fixed amount of the second eluent accumulated in the second flow path directional valve is connected to a pathway leading to the first flow path directional valve, control is carried out that supplies the first eluent in a state in which a remainder of the second eluent is allowed to remain in the injection loop and a pathway different from the injection loop is connected to the pathway leading to the first flow path directional valve, after the first eluent has been supplied to the injection loop until a portion of a fixed amount of the second eluent is discharged from the injection loop.

In a preferred embodiment of the present invention, the eluent supplier is provided with a fixed displacement pump that supplies the first eluent to the second flow path directional valve.

In a preferred embodiment of the present invention, blood is used for the specimen, with an object being to measure glycohemoglobin.

Liquid chromatography provided by a second aspect of the present invention has: a step of preparing a sample from a specimen; a step of supplying the sample to a column through a first flow path directional valve; a step of supplying as a mobile phase two or more types of eluent to the column through the first flow path directional valve; a step of supplying a test solution composed of components of the sample separated by the column and the eluent to an analyzer; and a step of measuring absorbance of the test solution by the analyzer, wherein the two or more types of eluent are supplied to the first flow path directional valve in an unmixed state.

In a preferred embodiment of the present invention, a step is further provided for washing the column by supplying to the column at least a portion of a fixed amount of the second eluent accumulated in a second flow path directional valve connected to the first flow path directional valve and the first eluent subsequently introduced into the second flow path directional valve from a port different from that of the second eluent through the first flow path directional valve either during or after the step of measuring absorbance.

In a preferred embodiment of the present invention, in the washing step, in a state in which an injection loop for retaining the fixed amount of the second eluent accumulated in the second flow path directional valve is connected to a pathway leading to the first flow path directional valve, the first eluent is continuingly supplied to the injection loop until all of the fixed amount of the second eluent is discharged from the injection loop.

In a preferred embodiment of the present invention, in the washing step, in a state in which an injection loop for retaining the fixed amount of the second eluent accumulated in the second flow path directional valve is connected to a pathway leading to the first flow path directional valve, the first eluent is supplied in a state in which a remainder of the second eluent is allowed to remain in the injection loop and a pathway different from the injection loop is connected to the pathway leading to the first flow path directional valve, after the first eluent has been supplied to the injection loop until a portion of a fixed amount of the second eluent is discharged from the injection loop.

In a preferred embodiment of the present invention, supplying of the first eluent to the second flow path directional valve is carried out by using a fixed displacement pump.

In a preferred embodiment of the present invention, blood is used for the specimen, with an object being to measure glycohemoglobin.

Other characteristics and advantages of the present invention will be made clear by the following detailed description with reference to the appended drawings.

BEST MODE FOR CARRYING OUT THE INVENTION

The following provides a detailed explanation of preferred embodiments of the present invention with reference to the drawings.

Figure 1:
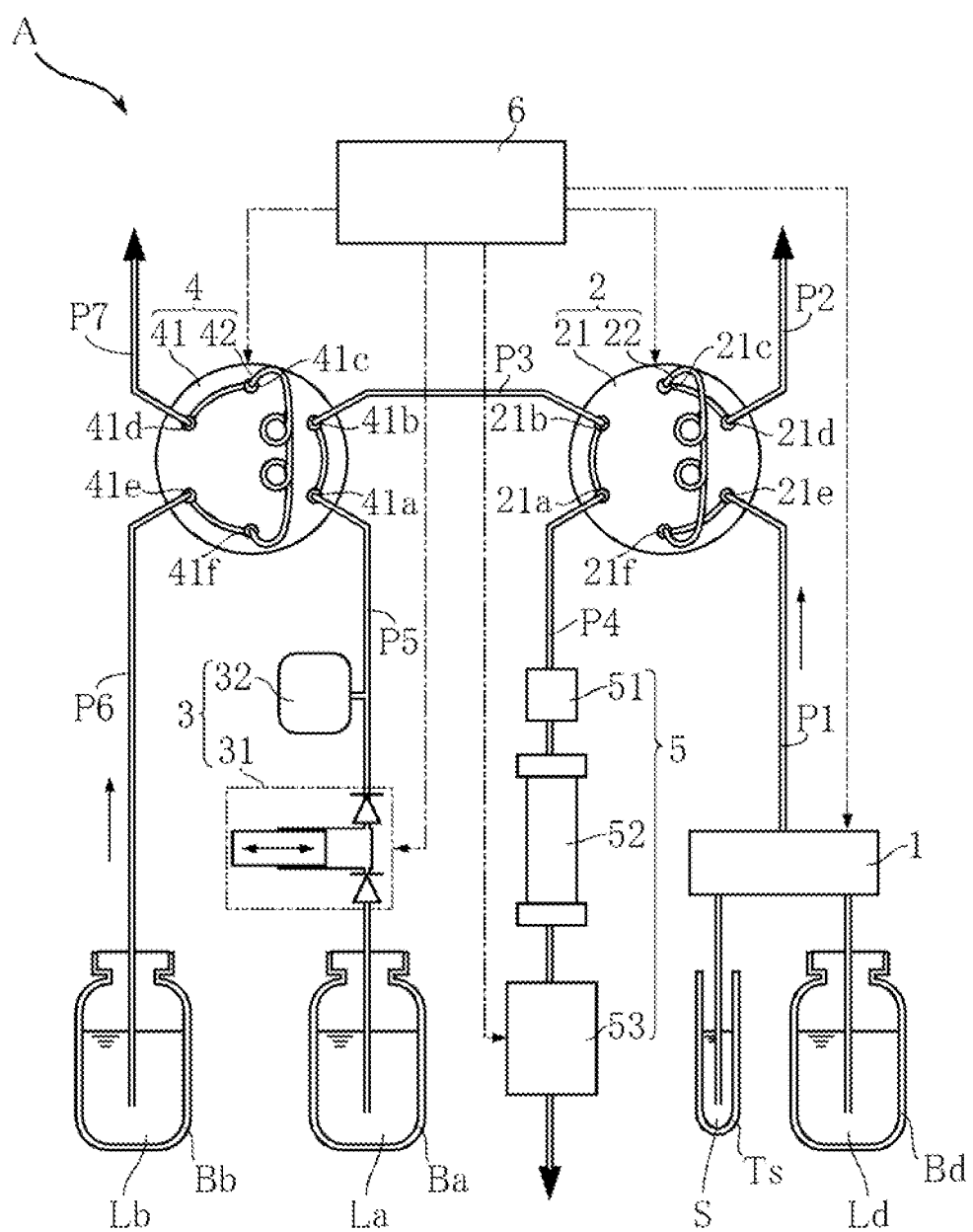
FIG. 1 is a system configuration diagram showing an example of a liquid chromatography apparatus according to the present invention.

FIG. 1 shows an example of a liquid chromatography apparatus according to the present invention. A liquid chromatography apparatus A of the present embodiment is provided with a sample preparation unit 1, a flow path directional valve 2, a feeder 3, a flow path directional valve 4, an analysis unit 5 and a controller 6. This liquid chromatography apparatus A carries out liquid chromatography on a specimen S such as blood.

The sample preparation unit 1 produces a sample on which liquid chromatography is to be carried out by diluting a prescribed amount of the specimen S collected from a blood vessel Ts to a prescribed factor with a diluent Ld collected from a bottle Bd. The sample preparation unit 1 includes, for example, a needle-shaped nozzle for collecting the specimen S from the blood vessel Ts, a collection tube for collecting the diluent Ld from the bottle Bd, and a stirrer that mixes these.

The flow path directional valve 2 has, for example, a 6-way valve 21 and an injection loop 22. The 6-way valve 21 has ports 21a, 21b, 21c, 21d, 21e and 21f, and rotates freely relative to the injection loop 22. The ports 21a, 21b, 21c and 21d and the ports 21e and 21f are respectively linked by mutually independent flow paths. In the state shown in the drawing, the port 21a is connected to a pipe P4, the port 21b is connected to a pipe P3, the ports 21c and 21f are connected to the injection loop 22, the port 21d is connected to a pipe P2, and the port 21e is connected to the sample preparation unit 1 through a pipe P1. The injection loop 22 is for accumulating a fixed amount of the sample. In the present embodiment, the volume of the injection loop 22 is made to be, for example, about 3.4 µL.

The feeder 3 and the flow path directional valve 4 compose an eluent supplier as referred to in the present invention. The feeder 3 is for delivering or feeding an eluent La housed in a bottle Ba to the flow path directional valve 4, and is provided in a pipe P5. The feeder 3 is composed of a plunger pump 31 and a damper 32. The plunger pump 31 employs a structure provided with a reciprocating plunger and a check valve, and is equivalent to an example of a fixed displacement pump. The damper 32 fulfills the function of alleviating pulsation generated by the plunger pump 31.

The flow path directional valve 4 has, for example, a 6-way valve 41 and an injection loop 42. The 6-way valve 41 has ports 41a, 41b, 41c, 41d, 41e and 41f, and rotates freely relative to the injection loop 42. The ports 41a, 41b, 41c and 41d and the ports 41e and 41f are respectively linked by mutually independent flow paths. In the state shown in the drawing, the port 41a is connected to the feeder 3 through the pipe P5, the port 41b is connected to the flow path direction valve 2 through the pipe P3, the ports 41c and 41f are connected to the injection loop 42, the port 41d is connected to a pipe P7, and the port 41e is connected to a bottle Bb housing an eluent Lb through a pipe P6. In the present embodiment, the eluent Lb has a higher salt concentration than the eluent La. The injection loop 42 is for accumulating a fixed amount of the eluent Lb. In the present embodiment, the volume of the injection loop 42 is made to be, for example, about 142 µL. This is equivalent to an amount delivered for 5 seconds by the feeder 3.

The analysis unit 5 is connected to the flow path directional valve 2 through the pipe P4, and is the site where analysis by liquid chromatography is carried out. The analysis unit 5 is composed of a pre-filter 51, a column 52 and a photometric unit 53. The pre-filter 51 prevents unwanted substances from entering the column 52. The column 52 retains a filler for adsorbing the introduced sample. After the sample has been adsorbed onto the filler, when the eluent La is injected into the column 52, the adsorbed sample is desorbed by the eluent La. Moreover, the desorbed sample and the eluent La flow through the column 52 and are discharged as an eluate. The photometric unit 53 is composed so as to analyze components of the sample by, for example, measuring absorbance of the eluate flowing from the column 52, and is equivalent to one example of analyzers referred to in the present invention.

The controller 6 respectively drives and controls the sample preparation unit 1, the flow path directional valve 2, the feeder 3, the flow path directional valve 4 an the analysis unit 5, and is composed of, for example, a CPU, a memory and an interface for transmitting and receiving signals. The controller 6 controls processing for carrying out analysis of the sample as described below as well as subsequent analyses.

Next, an explanation is provided of analysis using the liquid chromatography apparatus A with reference to FIGS. 1 to 10.

Figure 2:
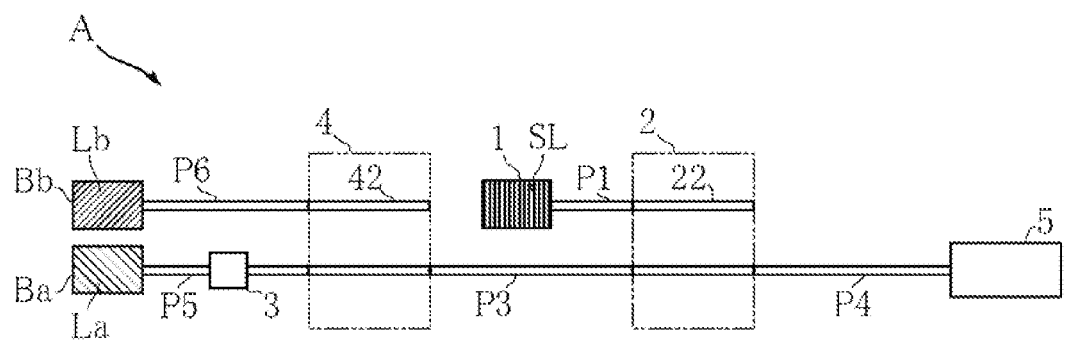
FIG. 2 is a conceptual drawing showing a flow path of the liquid chromatography apparatus shown in FIG. 1.

First, the liquid chromatography apparatus A is in an initial analysis state shown in FIGS. 1 and 2. FIG. 2 is schematically represents flow paths of the liquid chromatography apparatus A. In these drawings, a sample SL is prepared by diluting the specimen S with the diluent Ld in the sample preparation unit 1.

Figure 3:
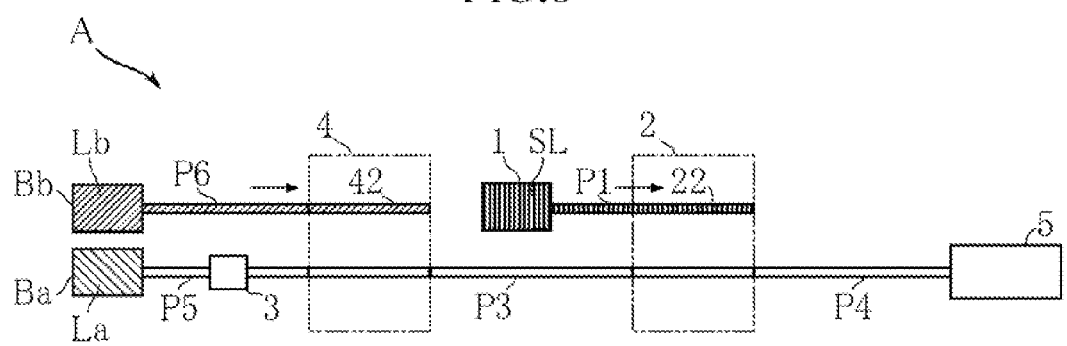
FIG. 3 is a conceptual drawing showing a state in which an eluent has been introduced into an injection loop in the liquid chromatography apparatus shown in FIG. 1.

Next, as shown in FIGS. 1 and 3, the sample SL is introduced into the injection loop 22. This injection is carried out by, for example, an aspiration pump (not shown) arranged downstream from the pipe P2. In addition, at this time, the eluent Lb is introduced into the injection loop 42. This injection is carried out by, for example, an aspiration pump (not shown) arranged downstream from the pipe P7. As a result of the introduction thereof, a fixed amount of the sample SL is accumulated in the injection loop 22, and a fixed amount of the eluent Lb is accumulated in the injection loop 42.

Figure 4:
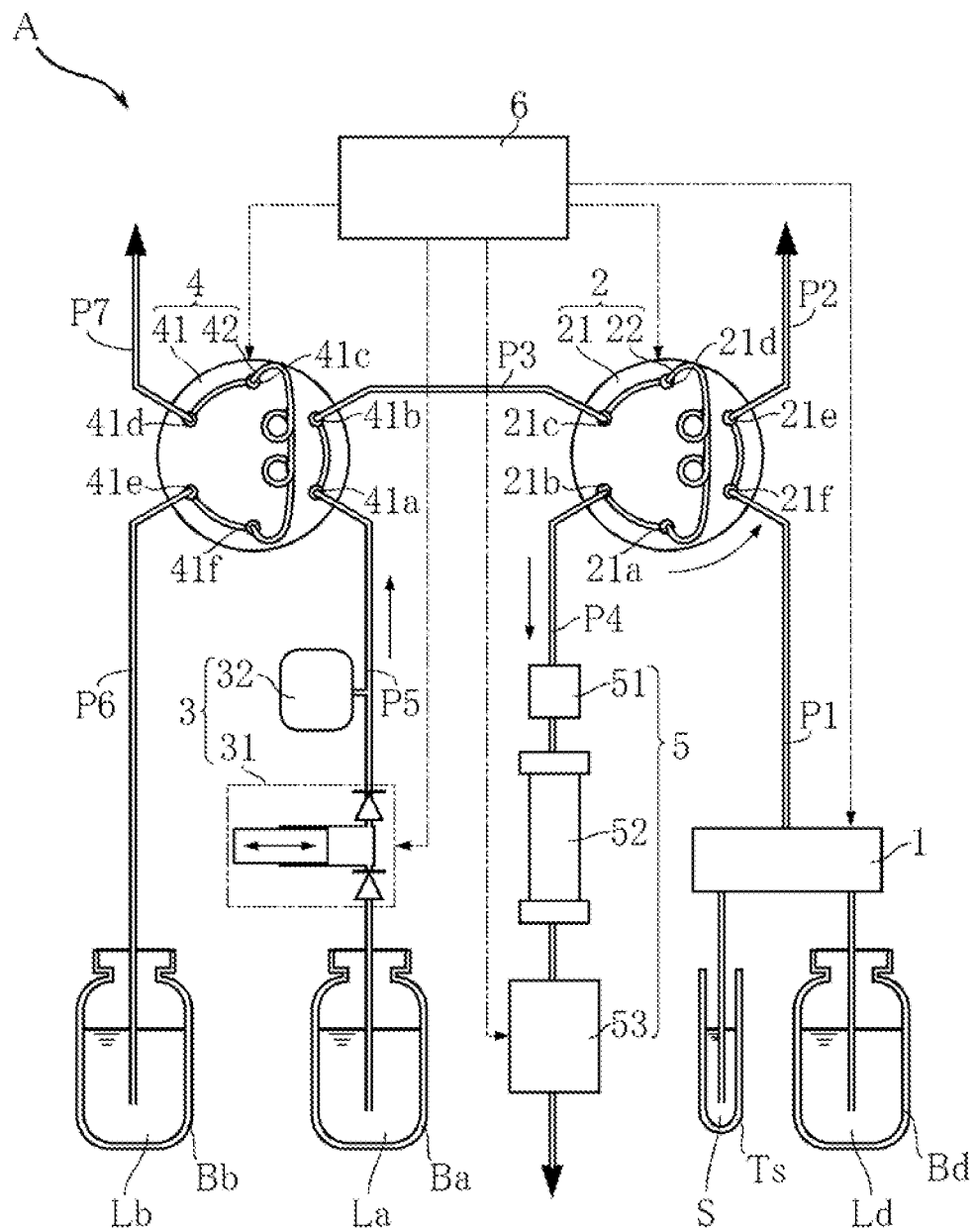
FIG. 4 is a system configuration diagram showing a state in which a six-way valve has been rotated in the liquid chromatography apparatus shown in FIG. 1.
Figure 5:
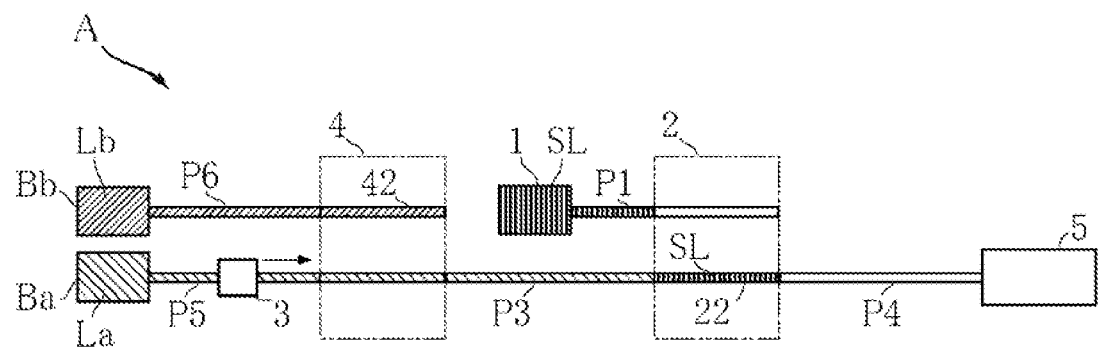
FIG. 5 is a conceptual drawing showing a state in which a six-way valve has been rotated in the liquid chromatography apparatus shown in FIG. 1.
Figure 6:
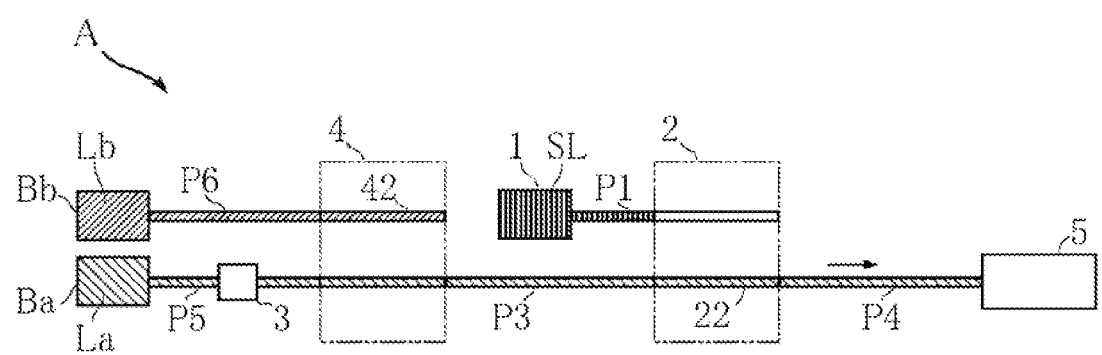
FIG. 6 is a conceptual drawing showing delivery of an eluent in the liquid chromatography apparatus shown in FIG. 1.

Next, as shown in FIG. 4, the 6-way valve 21 of the flow path directional valve 2 is rotated by, for example, 60° in the counter-clockwise direction. As a result, the ports 21a and 21d are connected to the injection loop 22, the port 21b is connected to the pipe P4, the port 21c is connected to the port P3, the port 21e is connected to the pipe P2, and the port 21f is connected to the pipe P1. By then driving the plunger pump 31 while in this state, the eluent La is delivered from the feeder 3 to the flow path directional valve 4. This eluent La moves toward the flow path directional valve 2 as shown in FIG. 5 through the ports 41a and 41b and the pipe P3. As shown in FIG. 6, a fixed amount of the sample SL accumulated in the injection loop 22 with the eluent La is sent to the analysis unit 5. In the analysis unit 5, a specific component contained in the sample SL is analyzed by the photometric unit 53.

In the state in which this analysis is still in progress or has been completed, other components not targeted for analysis other than the specific component targeted for analysis are adhered to the column 52, for example. These other components are not required for measurement results during analysis or inhibit subsequent analyses. Consequently, the controller 6 carried out control so these other components are eluted and washed out.

Figure 7:
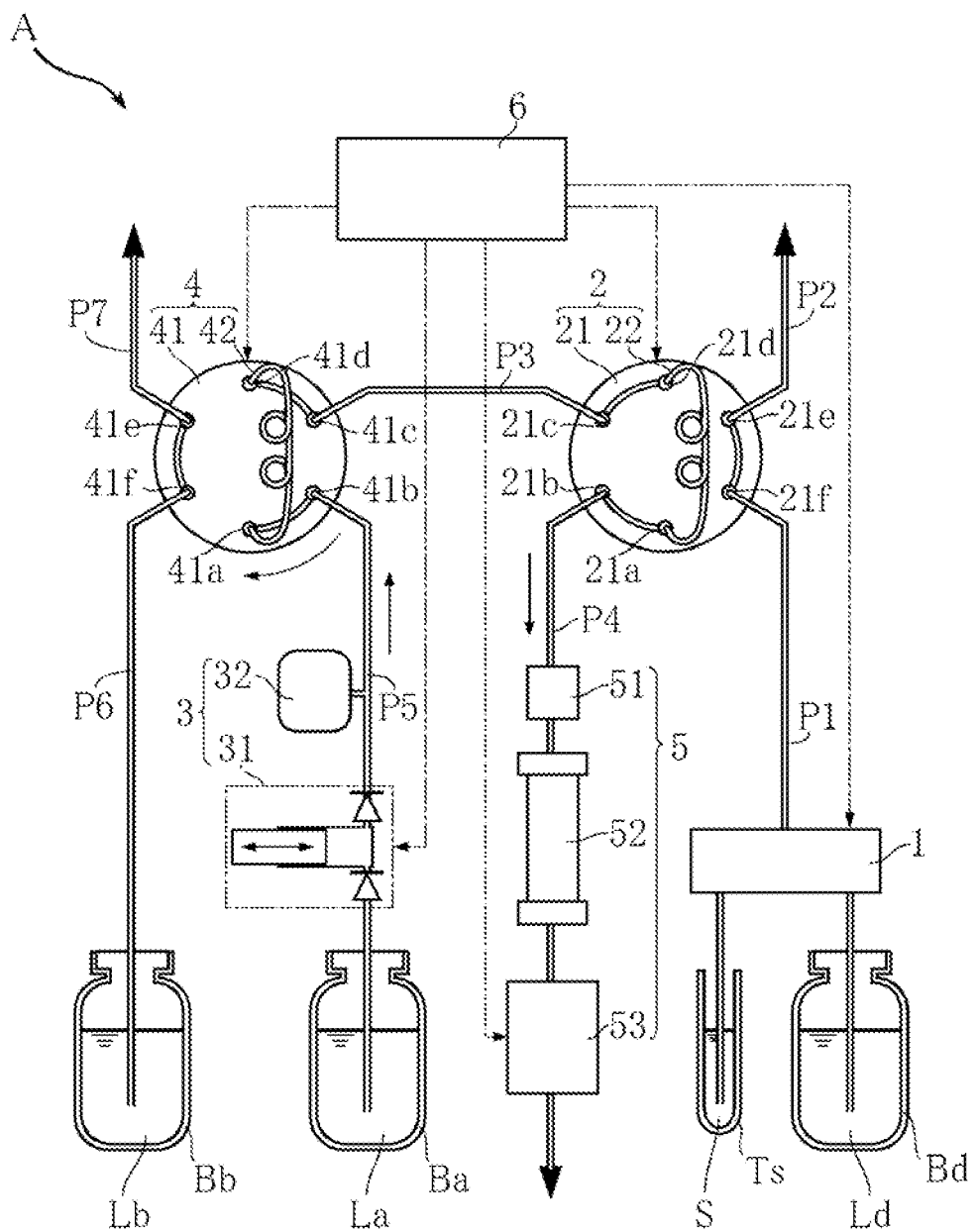
FIG. 7 is a system configuration diagram showing a state in which a 6-way valve has been rotated in the liquid chromatography apparatus shown in FIG. 1.

Namely, as shown in FIG. 7, the 6-way valve 41 of the flow path directional valve 4 is rotated by, for example, 60° in the clockwise direction. As a result, the ports 41a and 41d are connected to the injection loop 42, the port 41b is connected to the pipe P5, the port 41c is connected to the pipe P3, the port 41e is connected to the pipe P7, and the port 41f is connected to the pipe P6, resulting in the state shown in FIG. 8. By driving the plunger pump 31 while in this state, the eluent La is delivered from the feeder 3 towards the flow path directional valve 4. Whereupon, a fixed amount of the eluent Lb accumulated in the injection loop 42 is delivered to the pipe P3. This eluent Lb is then disposed between the eluent La that had been in the pipe P3 and the eluent La that has been sent by the feeder 3.

Figure 9:
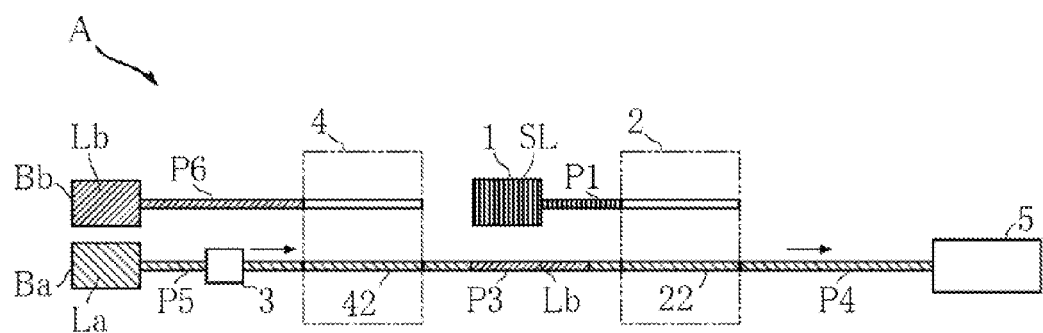
FIG. 9 is a conceptual drawing showing delivery of an eluent in the liquid chromatography apparatus shown in FIG. 1.

By continuing to further drive the plunger pump 31, the entire fixed amount of the eluent Lb is delivered from the injection loop 42 to the pipe P3 as shown in FIG. 9. Subsequently, by continuing delivery of the eluent La with the feeder 3, other components adhered to the column 52 are eluted and washed out by the eluent Lb, and as a result of further adequately filling the system, including the column 52, with the eluent La, the column 52 and the like are made to have a salt concentration suitable for carrying out the next analysis.

Next, an explanation is provided of the action of the liquid chromatography apparatus A and liquid chromatography of the present embodiment.

Figure 10:
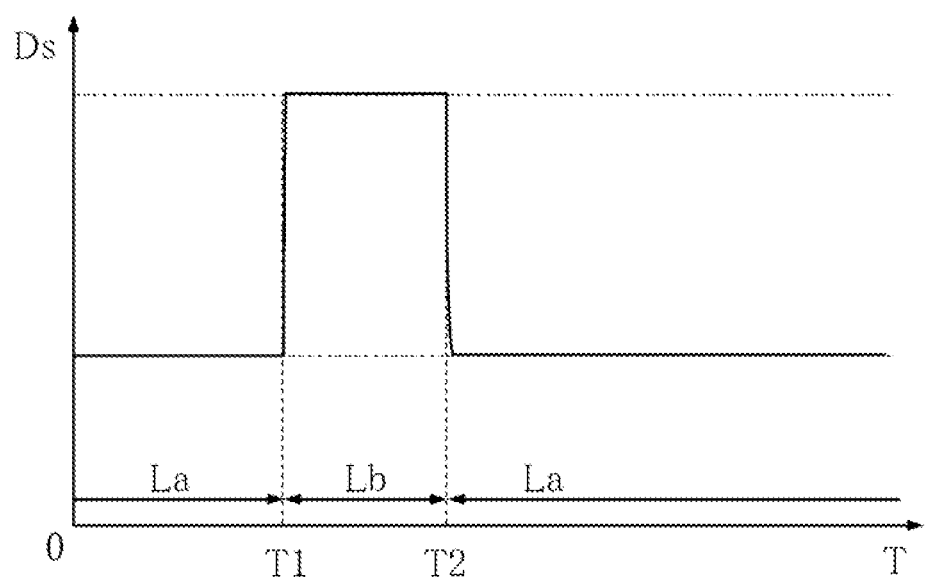
FIG. 10 is a graph indicating hysteresis of a column salt concentration in the liquid chromatography apparatus shown in FIG. 1.

FIG. 10 indicates hysteresis of the salt concentration Ds of the column 52 in processing for the analysis described above and the next analysis. The time T1 is the time at which the leading end of the eluent Lb shown in FIG. 9 has reached the column 52, while the time T2 is the time at which the trailing end of the eluent Lb has reached the column 52. The salt concentration Ds changes abruptly at either of these times T1 and T2, and changes to the salt concentration of the eluent La or Lb, respectively. The following provides a description of the reason for this.

Figure 8:
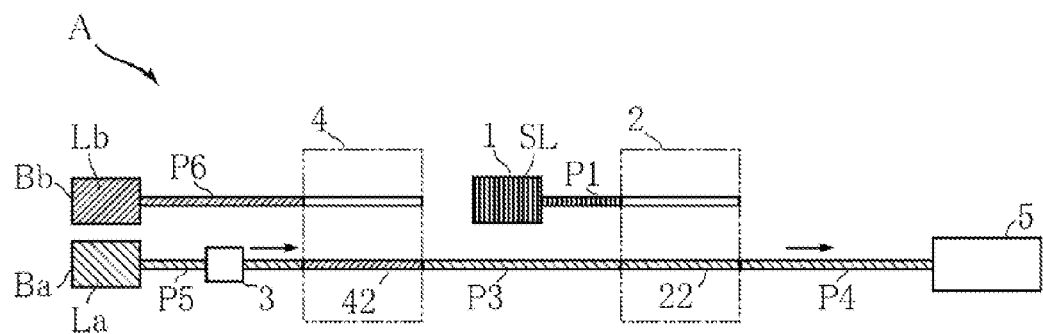
FIG. 8 is a conceptual drawing showing a state in which a 6-way valve has been rotated in the liquid chromatography apparatus shown in FIG. 1.
Figure 14:
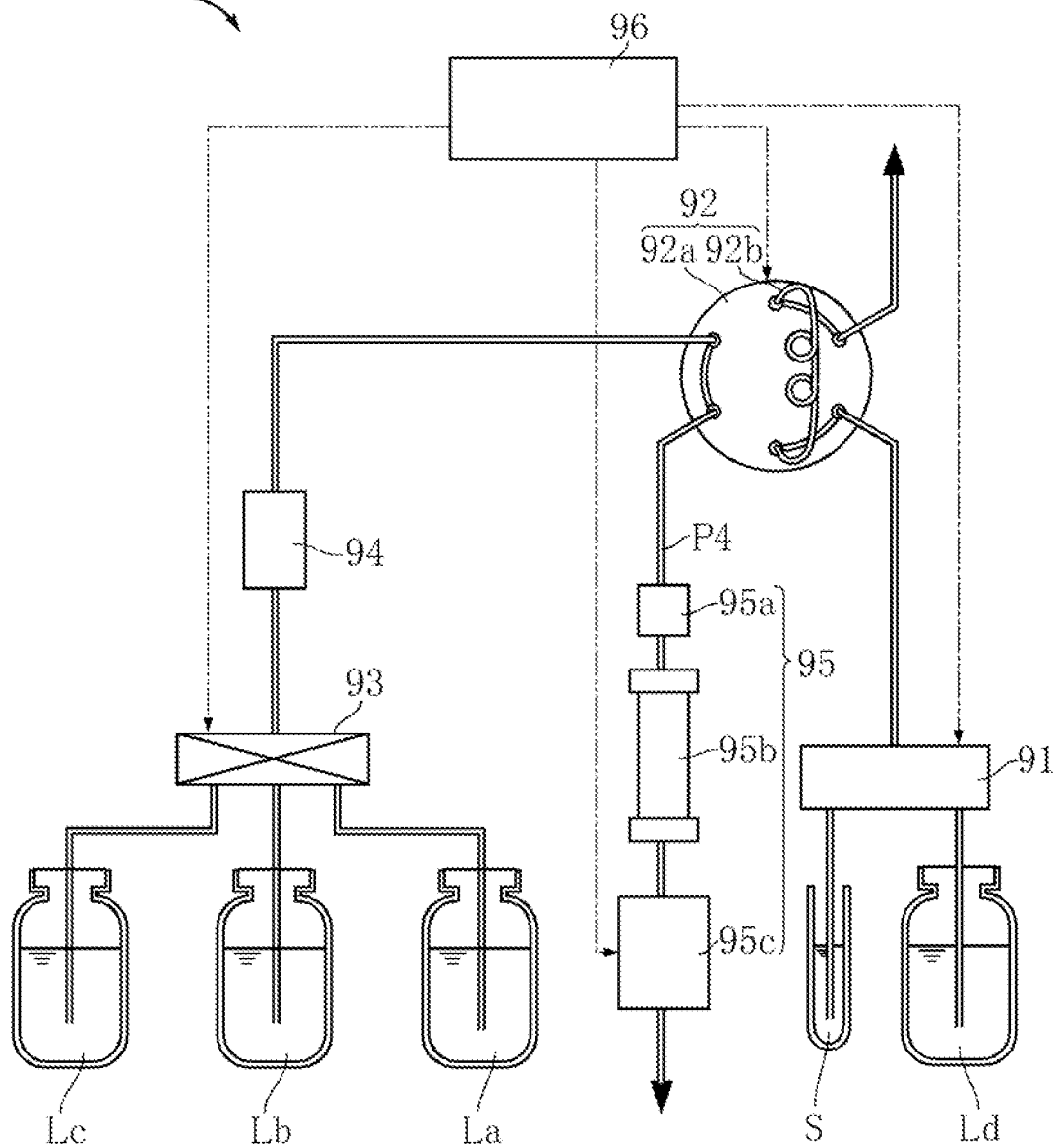
FIG. 14 is a system configuration diagram showing an example of a liquid chromatography apparatus of the prior art; and, FIG. 15 is a graph indicating hysteresis of salt concentration in a column of the liquid chromatography apparatus shown in FIG. 14.
Figure 15:
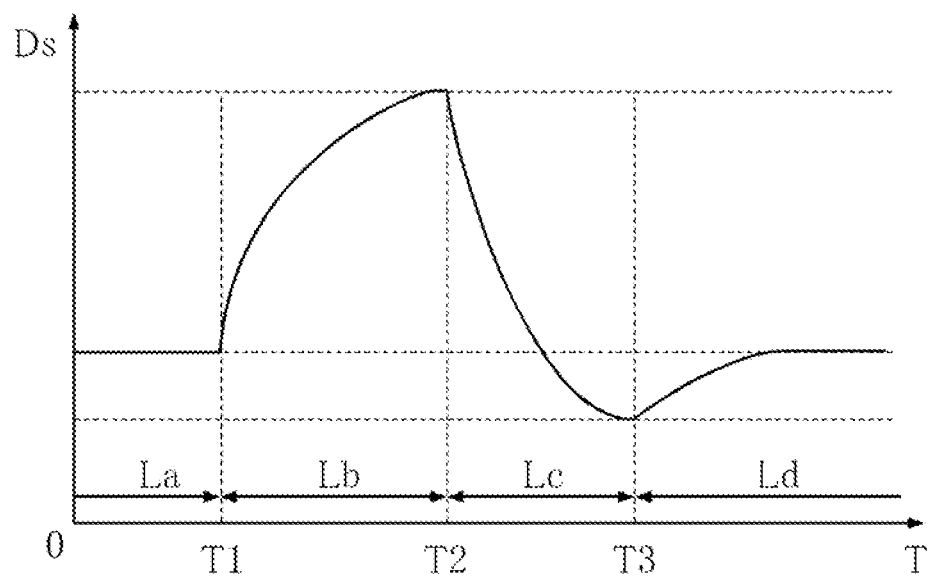

First, the eluents La and Lb are supplied to the flow path directional valve 4 from separate ports. Consequently, there is no mutual mixing whatsoever in the flow path leading to the flow path directional valve 4. Next, a fixed amount of the eluent Lb is introduced into the eluent La due to rotation of the 6-way valve 41 as shown in FIGS. 7 and 8. In this case, there is only the possibility of the mutual ends of the eluent La and the eluent Lb mixing in an extremely narrow flow path consisting of the pipe P3 and the injection loop 42. The degree of this mixing is much smaller than the mixing in, for example, the manifold 93 and the feed pump 94 shown in FIG. 14. As a result, the eluent Lb is supplied to the column 52 in a state of being surrounded by the eluent La without the occurrence of excessive mixing. Thus, the salt concentration Ds at the time T1 and the time T2 can be made to change abruptly as shown in FIG. 10.

If it is possible to abruptly change salt concentration in the column 52 in this manner, it is not necessary to allow a lengthy amount of time to pass until the salt concentration Ds returns to a desired concentration (salt concentration of the eluent La). In addition, in the present embodiment, differing from the use of three types of eluents La, Lb and Lc as in the prior art, only two types of eluents La and Lb are used. Thus, it becomes possible to rapidly return the system, including the column 52, to a state suitable for carrying out the next analysis, thereby making it possible to shorten analysis time of liquid chromatography. In addition, this also serves to reduce consumption of eluent.

Figure 11:
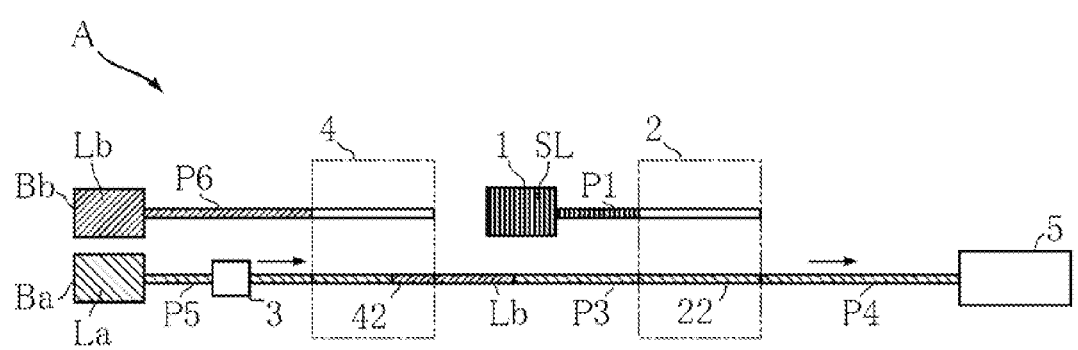
FIG. 11 is a conceptual drawing showing delivery of an eluent in another example of liquid chromatography using the liquid chromatography apparatus shown in FIG. 1.
Figure 12:
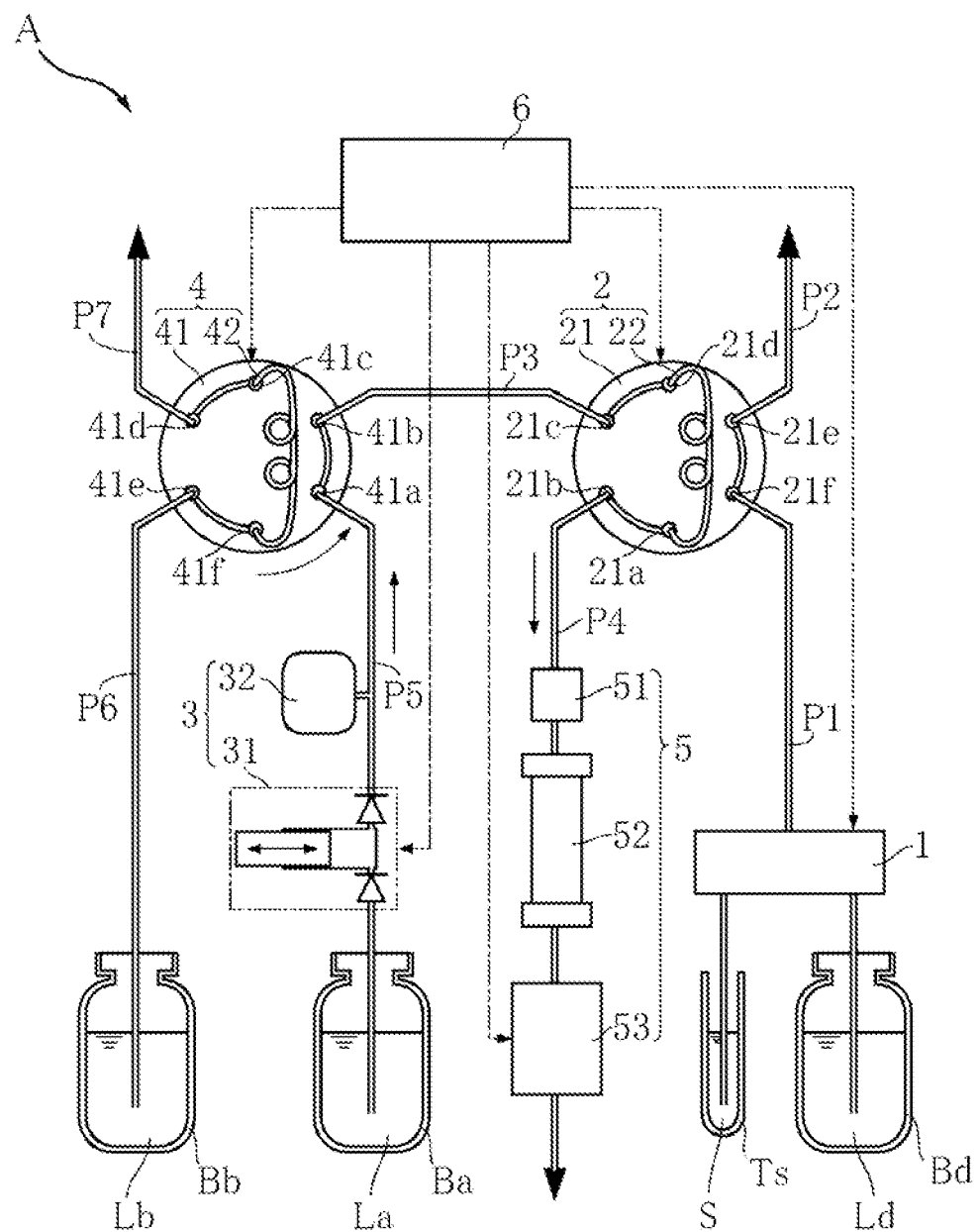
FIG. 12 is a system configuration diagram showing a state in which a 6-way valve has been rotated in another example of liquid chromatography using the liquid chromatography apparatus shown in FIG. 1.
Figure 13:
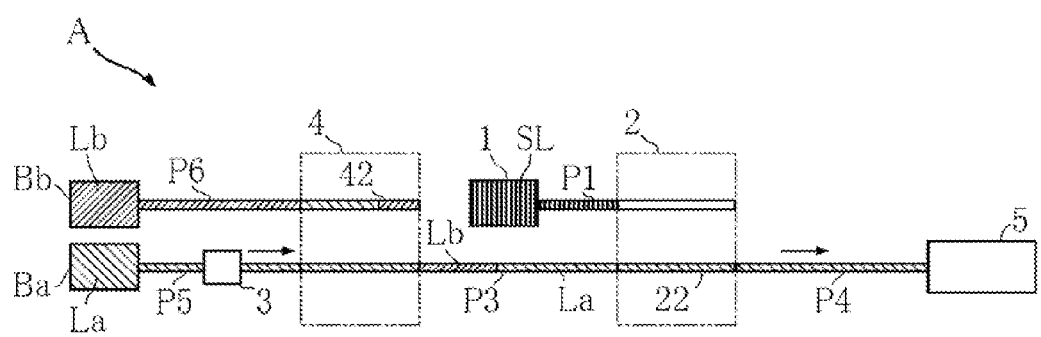
FIG. 13 is a conceptual drawing showing delivery of an eluent in another example of liquid chromatography using the liquid chromatography apparatus shown in FIG. 1.

FIGS. 11 to 13 show another embodiment of the liquid chromatography according to the present invention. Furthermore, in these drawings, those elements that are identical or similar to the previously described embodiment are indicated with the same reference symbols as the previous embodiment. In the present embodiment, the controller 6 of the liquid chromatography apparatus A carries out control in a different manner from the previously described embodiment with respect to processing for carrying out the next analysis.

First, processing for carrying out the analysis indicated in FIGS. 1 to 8 and the next analysis is carried out. Next, the eluent La is delivered by the feeder 3 from the state shown in FIG. 8. During this delivery, delivery of the eluent La continues until a portion of a fixed amount of the eluent Lb accumulated in the injection loop 42 is discharged from the injection loop 42 as shown in FIG. 11. More specifically, the plunger of the plunger pump 31, which is a type of fixed displacement pump, is reciprocated a prescribed number of times. Since the amount of the eluent La that is delivered during one reciprocation of this plunger is constant (for example, 28 μL), the amount of the eluent La that is delivered when this plunger is reciprocated a prescribed number of times is also constant.

The 6-way valve 41 of the flow path directional valve 4 is then rotated by, for example, 60° in the counter-clockwise direction from the state shown in FIG. 11 as shown in FIG. 12. The eluent La continues to be delivered by the feeder 3. At this time, as shown in FIG. 13, the eluent Lb discharged from the injection loop 42 is surrounded by the eluent La. Subsequently, by further continuing to deliver the eluent La with the feeder 3, other components adhered to the column 52 are eluted and washed out by the eluent Lb, and as a result of further adequately filling the system, including the column 52, with the eluent La, the column 52 and the like are made to have a salt concentration suitable for carrying out the next analysis.

According to the present embodiment as well, hysteresis of the salt concentration Ds in the column 52 can be made to resemble the hysteresis shown in FIG. 10, and the analysis time of liquid chromatography can be shortened. In particular, switching between the trailing end of the eluent Lb and the following eluent La is carried out by rotation of the 6-way valve 41 of the flow path directional valve 4. Consequently, contact time between the trailing end of the eluent Lb and the eluent La can be shortened to a greater degree than the case shown in FIGS. 8 and 9. As a result, mixing between the trailing end of the eluent Lb and the eluent La can be further inhibited, which is preferable for shortening analysis time.

In addition, since the 6-way valve 41 is rotated before the entire fixed amount of the eluent Lb accumulated in the injection loop 42 is discharged after other components not targeted for analysis were able to be eluted, the amount of the eluent Lb sent to the column 52 is even less than the amount in the previously described embodiment. As a result, the amount of time from the time T1 to the time T2 can be further shortened, which is preferable for shortening analysis time.

By using the plunger pump 31 that is a type of fixed displacement pump, the amount of the eluent Lb discharged from the injection loop 42 in FIG. 11 can be accurately determined by counting the number of times the plunger reciprocates. This offers the advantage of being able to supply an amount of the eluent Lb that is adequate for eluting and washing out the other components described above while also being the minimum required amount of the eluent Lb from the viewpoint of shortening analysis time.

The liquid chromatography apparatus and liquid chromatography according to the present invention are not limited to the previously described embodiments. The design of specific configurations of the liquid chromatography apparatus and liquid chromatography according to the present invention can be modified in various ways as desired.

The first and second eluents referred to in the present invention are not limited to those having mutually different salt concentrations, but rather, those having mutually different hydrogen ion concentration indices (pH), for example, may also be used.

The invention claimed is:

1. A liquid chromatography apparatus, comprising:
   a sample preparation unit for preparing a sample from a specimen;
   a column configured to separate components of the sample;
   an eluent supplier for supplying as a mobile phase two or more types of eluent to the column;
   a first flow path directional valve capable of introducing a fixed amount of the sample to the column and capable of introducing the eluent to the column;

an analyzer for analyzing a test solution composed of the sample components separated by the column and the eluent; and a controller for controlling operation of the sample preparation unit, the eluent supplier, the first flow path directional valve and the analyzer;

wherein the eluent supplier is provided with a second flow path directional valve for supplying, to the first flow path directional valve, first and second eluents mutually supplied to separate ports of the second flow path directional valve, said second flow path directional valve includes an injection loop for retaining the fixed amount of the second eluent and the second flow path directional valve is rotatable, and the controller is configured to cause a fixed amount of the second eluent to be accumulated in the second flow path directional valve at least through controlling the rotation of the second flow path directional valve, and also cause the first eluent to be introduced into the second flow path directional valve from a port different from that of the second eluent, whereby at least a portion of the fixed amount of the second eluent and subsequently the first eluent are supplied from the second flow path directional valve to the column through the first flow path directional valve.

2. The liquid chromatography apparatus according to claim 1, wherein the eluent supplier is provided with a fixed displacement pump for supplying the first eluent to the second flow path directional valve.

\* \* \* \* \*